US006569839B1

(12) United States Patent  
McKay (10) Patent No.: US 6,569,839 B1
(45) Date of Patent: May 27, 2003

(54) FAST-ACTING PHARMACEUTICAL COMPOSITIONS AND METHODS OF USE

(76) Inventor: Douglas William McKay, 450 Moosa Blvd., Suite C, Eunice, LA (US) 70535

( * ) Notice: Subject to any disclaimer, the term of this patent is extended or adjusted under 35 U.S.C. 154(b) by 0 days.

(21) Appl. No.: 09/449,637

(22) Filed: Nov. 30, 1999

Related U.S. Application Data (63) Continuation-in-part of application No. 09/154,520, filed on Sep. 16, 1998, now Pat. No. 6,325,788.

(51) Int. Cl.$^7$ ................ A61K 31/727; A61K 31/56; A61K 31/43; A61K 31/40
(52) U.S. Cl. ................ 514/54; 514/56; 514/59; 514/169; 514/198; 514/411; 514/818; 514/887
(58) Field of Search ................ 514/54, 56, 59, 514/169, 198, 411, 818, 887

(56) References Cited

U.S. PATENT DOCUMENTS

| | | | | |
|---|---|---|---|---|
| 2,441,498 A | | 5/1948 | Löfgren et al. | 260/562 |
| 2,483,871 A | | 10/1949 | Bartz | 260/562 |
| 2,483,884 A | | 10/1949 | Crooks, Jr. et al. | 260/562 |
| 2,483,892 A | | 10/1949 | Ehrlich et al. | 195/80 |
| 2,602,769 A | | 7/1952 | Murray et al. | 195/51 |
| 2,884,358 A | | 4/1959 | Bush et al. | 167/74 |
| 4,478,822 A | * | 10/1984 | Haslam et al. | 424/78 |
| 4,879,274 A | | 11/1989 | Kamiya et al. | 514/12 |
| 4,983,586 A | | 1/1991 | Bodor | 514/58 |
| 5,024,998 A | | 6/1991 | Bodor | 514/58 |
| 5,616,121 A | | 4/1997 | McKay | 604/35 |
| 5,700,485 A | | 12/1997 | Berde et al. | 424/501 |
| 5,770,222 A | | 6/1998 | Unger et al. | 424/450 |
| 5,875,776 A | * | 3/1999 | Vaghefi | 128/203.15 |

FOREIGN PATENT DOCUMENTS

| | | |
|---|---|---|
| EP | 0 401 016 A1 | 5/1990 |
| EP | 0 513 858 A2 | 11/1992 |
| FR | 74.05574 | 2/1974 |
| GB | 2 262 165 A | 7/1991 |
| WO | WO 86-01412 | 3/1986 |
| WO | WO 87/00759 | 2/1987 |
| WO | WO 91/12830 | 9/1991 |

* cited by examiner

Primary Examiner—Raymond Henley, III
Assistant Examiner—Donna Jagoe
(74) Attorney, Agent, or Firm—McDermott, Will & Emery (57) ABSTRACT

A pharmaceutical composition comprising at least one local anesthetic, at least one anti-inflammatory agent and at least one antibiotic are disclosed. The local anesthetic has a peak effect no later than about 10 minutes after administration to a mammal, and the anesthetic and anti-inflammatory have a half-life of no greater than about 36 hours after administration. The pharmaceutical composition, thus, advantageously provides rapid relief of pain with a substantially low residual accumulation of active components so that the pharmaceutical composition can be repeatedly or continuously administered to a wound. Embodiments include preparing a medicinal solution including Lidocaine as the local anesthetic, Hydrocortisone sodium succinate as the anti-inflammatory agent, Chloramphenicol as the antibiotic agent and, optionally, Heparin as an anticoagulant. The medicinal solution is continuously administered to treat a wound of a mammal to maintain a constant positive physiological pressure in the treated wound at a pressure to enable permeation of the medicinal solution and fluids from the wound with concomitant periodical suctioning of debris from the wound.

6 Claims, 5 Drawing Sheets

FAST-ACTING PHARMACEUTICAL COMPOSITIONS AND METHODS OF USE

CROSS-REFERENCE TO RELATED APPLICATIONS

This application is a continuation-in-part of application U.S. Ser. No. 09/154,520 filed Sep. 16, 1998 now U.S. Pat. No. 6,325,788 titled TREATMENT OF WOUND OR JOINT FOR RELIEF OF PAIN AND PROMOTION OF HEALING, the entire disclosure of which is hereby incorporated by reference herein.

TECHNICAL FIELD

The present invention relates to pharmaceutical compositions useful for the treatment of a wound or joint, with particular applicability to post operative closed muscular skeletal wounds. The pharmaceutical composition provides alleviation of pain, while promoting healing of the wound and early rehabilitation.

BACKGROUND

Of major concern in the care of wounds, such as incurred in joint surgery, are relief of post-operative pain, avoidance of infection, hastening of healing, early joint motion, and a decrease in the length of necessary hospital services. Traditional post-operative management of orthopaedic wounds or traumatic wounds have varied in approach. However, an important consideration in the management of wounds is to prevent the painful accumulation of blood and debris and to prevent infection following the formation of an open wound.

Pain relief and reduced swelling can be minimized by leaving a surgical wound or traumatic wound open thereby encouraging the free flow of debris and accumulated fluid out of the wound. Irrigation of the open wound with a sterile solution further promotes the removal of debris, blood, extra-cellular fluid, etc. The same debris and blood in an open wound, however, provide an excellent culture medium for bacterial growth and, hence, such techniques invite infection and promote contamination. Wound closure, conversely, prevents the beneficial flow of debris and fluid from the wound with concomitant pain relief but advantageously reduces the occurrence of bacterial infection and otherwise exterior contamination.

Conventional post-operative management of wounds have sought the benefits of both techniques by closing the wounds but maintaining a drainage tube from the wound through the skin. Closed wound drainage systems, however, have not eliminated infections. The tube can be under no external pressure or vacuum thereby permitting the natural flow of bodily fluids. Since the body does not produce a constant flow of fluid, an open drain tube technique still provides a avenue for infection and contamination.

Moreover, complete removal of debris can be difficult with the sole use of a drain tube. To assist in the removal of debris and fluid from a wound, vacuum drainage systems have been developed to create a negative pressure in the wound. However, vacuum drains have a tendency to promote a flow of contaminates from the skin edges around the tube and back in to the wound. Accordingly, a need exists for an improved system of managing debris and fluid removal from a wound while maintaining a sterile environment.

In addition to the removal of contamination and debris from a wound, post operative management of wounds requires the relief of pain and rehabilitation. Conventionally, pain is treated by the administration of narcotics and/or analgesia to the wound. The treatment of pain relief by means of narcotics, however, has drawbacks such as constipation, drowsiness, stasis pneumonitis, itching, vomiting, confusion and ataxia. Problems associated with epidural analgesia include itching, constipation, increased blood loss, severe ataxia and very expensive multiple injections. Thus, a need exists for new and improved methods for managing pain relief and maintaining a sterile environment.

U.S. Pat. No. 5,616,121, issued to McKay on Apr. 1, 1997, discloses a treatment for alleviating pain in joint wounds through the use of irrigation with a medicinal solution. Irrigation lessens the risk of infection and scar tissue that would otherwise occur from accumulated debris and fluid. The disclosed treatment provides an infusion tubing for infusing a prepared solution into the wound, and a suction tubing for suctioning fluids from the wound. The infusion tubing and suction tubing are joined to communicate with a single tube that is inserted in the wound. Through the use of valves and a controlled pump operation, successive timed intervals of infusion and suction, separated by interruption intervals, bathing of the wound is achieved.

There are several important criteria for use of medical devices in post operative care management of wounds. The risk of adverse health or adverse well being of the patient should be insignificant. Any device that is connected internally to the patient to infuse or subtract fluid should be a closed, sterile system to prevent invasion of environmental contaminants. As patients should be ambulatory as early as possible to prevent deep vein thrombosis, the device should be portable, thereby permitting patient mobility. Mobility also enhances the prospects of early rehabilitation and shortened hospital stay. The administration of drugs for pain relief should have minimal side effects and promote healing.

A continuing need, therefore, exists for a system of managing a post-operative wound which relieves the accumulation of fluid, alleviates or minimizes pain and promotes healing and early rehabilitation.

SUMMARY OF THE INVENTION

An advantage of the present invention is a fast-acting, short-lived pharmaceutical composition. The pharmaceutical composition is advantageously capable of being repeatedly or continuously administered to a mammal over a period of time to relieve pain without toxic accumulation of the active ingredients in the mammal.

An additional advantage of the present invention is a medicinal solution capable of being repeatedly or continuously administered to a wound of a mammal which alleviates or minimizes pain and promotes healing and early rehabilitation.

These and other advantages are satisfied, at least in part, by the provision of a pharmaceutical composition comprising at least one local anesthetic, at least one anti-inflammatory agent and at least one antibiotic. In accordance with the present invention, the local anesthetic has a peak effect of no later than about 10 minutes, e.g. no later than about 5 minutes after, administration to a mammal, and the anesthetic and anti-inflammatory have a half-life of no greater than about 36 hours, e.g. no greater than about 8–12 hours, after administration to a mammal. The pharmaceutical composition, thus, advantageously provides rapid relief of pain with a substantially low residual accumulation of active components so that the pharmaceutical composition can be repeatedly or continuously administered to a wound. The pharmaceutical composition can further comprise an anticoagulant to alleviate or minimize detrimental clotting.

Embodiments of the present invention include a pharmaceutical composition comprising Lidocaine as the local anesthetic, Hydrocortisone sodium succinate as the anti-inflammatory agent, Chloramphenicol as the antibiotic agent and Heparin as the optional anticoagulant.

Another aspect of the present invention is a medicinal solution comprising about 0.01 to about 5 weight percent of a local anesthetic, about 0.01 to about 5 weight percent of an anti-inflammatory agent, about 0.01 to about 5 weight percent of an antibiotic, and a carrier, e.g. sterile water. The solution can optionally further include a sufficient amount of an anticoagulant to prevent clotting.

In accordance with the present invention, the medicinal solution can be intravenously, subcutaneously, or directly administered to a wound for treatment thereof. The medicinal solution can be repeatedly or continuously administered to maintain a relatively positive physiological pressure in the wound, e.g., up to about 50 mm/Hg, during and throughout the administration period. By maintaining a relatively positive physiological pressure in the wound, the administration of the medicinal solution enables permeation of the medicinal solution from within the wound to the surface of the wound and seepage therethrough. Seepage of the medicinal solution greatly enhances the process of relieving swelling, inflammation and contamination.

In an embodiment of the present invention, the medicinal solution is continuously and directly administered to the wound with periodic extraction or suction of fluid and/or debris from the wound. Thus, a post-operative joint wound can be cared for by maintaining a relatively positive physiological pressure in the wound during and throughout administration of the medicinal fluid to cause leaking of the infused medicinal solution throughout the wound and through the skin with periodic evacuation of fluid containing blood, debris, extracellular fluid, and/or contaminates thereby promoting early rehabilitation and the alleviation or minimization of pain.

Embodiments of the present invention include a solution comprising up to about 1250 mg of Lidocaine, up to about 400 mg of Hydrocortisone sodium succinate, up to about 1 gm of Chloramphenicol in about 1000 cc of normal saline solution and, optionally, about 1000 units of Heparin.

Additional advantages of the present invention will become readily apparent to those skilled in this art from the following detailed description, wherein only the preferred embodiment of the invention is shown and described, simply by way of illustration of the best mode contemplated of carrying out the invention. As will be realized, the invention is capable of other and different embodiments, and its several details are capable of modifications in various obvious respects, all without departing from the invention. Accordingly, the drawings and description are to be regarded as illustrative in nature, and not as restrictive.

BRIEF DESCRIPTION OF THE DRAWINGS

Reference is made to the attached drawings, wherein elements having the same reference numeral designations represent like elements throughout and wherein.

DETAILED DESCRIPTION OF THE INVENTION

The present invention overcomes the aforementioned disadvantages in part by its ability to mimic the normal defense of the human body to invasion by foreign material. The body has a normal tissue tension of 10–15 mm/Hg. A break in the skin will lead to swelling and increased tissue pressure. Wounds leak extra cellular fluid after bleeding has stopped due to the tissue tension, or pressure, that increases with inflammation and swelling. The leaking of cellular fluid in a wound relieves inflammation, swelling and pain in all layers through to the skin, while tending to prevent foreign materials from entering the wound.

In practicing the present invention, a post-operative wound is cared for by maintaining a relatively positive physiological pressure in the wound during and throughout the administration of a medicinal solution for a prescribed administration period. In an embodiment of the present invention, a closed wound irrigation system is provided wherein all infusion tubing will transport only the medicinal solution so that there is no mixing with body fluid or residue removed from the wound. A highly sterile environment thus can be provided and maintained at the wound. A concomitant advantage is that, without the possibility of such mixing, the medicinal solution can be infused throughout the irrigation period, during which time suction can be intermittently applied. The removal of fluids from the wound in accordance with the present invention eliminates or minimizes the build up of blood, dead tissue, debris, bacteria extra cellular fluids and further removes the residual short-lived agents in the infused medicinal solution.

In accordance with the present invention, an infusion tube is insertable into the wound for transporting a prepared medicinal solution to the joint. The prepared solution may contain prescribed amounts of at least one anesthetic, at least one anti-inflammatory, at least one antibiotic and, optionally, at least one anticoagulant in a saline mixture. A second tube is insertable into the wound for transport of fluid removed from the joint. The latter tube has perforations along the portion that is to be inserted in the wound to aid entry of the body fluids. A vacuum device is coupled to the second tube. Suction is automatically turned on to evacuate the wound for a prescribed period of time and then stopped for another prescribed period of time. The on/off cycle can be repeated, for example, up to about three days, e.g., over about a twenty four hour to about a seventy two hour period. In an embodiment of the present invention, the prepared medicinal solution is constantly administered directly into the wound during the entire prescribed period, i.e., continuously at a relatively constant rate of about 20 cc/hr to about 100 cc/hr of administration lasting up to about three days. The infusion tube and evacuation tube are isolated from each other to prevent entry of contaminants in to the wound. The on/off oscillation of the suction provides the advantage of pain alleviation as the cycle intervals are preadjusted to maintain a positive physiological pressure in the wound.

As a result, the administered medicinal solution, which has permeated the wound, can seep through to the skin in a manner that mimics the natural healing process of the body. Seepage of the medicinal solution greatly enhances the process of relieving swelling, inflammation and contamination. A plurality of preadjusted duty cycles are available, from which one may be selected as appropriate for the type of wound to be treated.

The vacuum device is typically a self-contained structure that includes a reservoir for receiving fluids evacuated from the wound and a section in which the vacuum apparatus and its control are housed. The reservoir is typically an enclosure having a top portion with at least one fluid inlet port and a bottom portion having at least one fluid outlet port. The bottom portion is sloped to facilitate drainage of fluid collected in the enclosure through the outlet port. The reservoir enclosure is structured to facilitate collection of blood received from the fluid input port. An inverted cone-shaped configuration may be employed extending from the bottom portion of the reservoir to a location in close proximity to this port to spread the blood near the entry of the reservoir and prevent damage to the collected blood cells. A filter surrounds the cone-shaped structure for filtering out particles, such as clots, from the received blood. The blood saving function occurs in an initial period following surgery. Collected blood is drained through the bottom output port. A vacuum release valve is typically provided at the top of the enclosure to preclude negative pressure in the reservoir while the blood is drained.

Preferably, an irrigation period then follows, the evacuated fluid being received through the other fluid input port. During the suction periods, negative pressure is created in the reservoir by a pump, which by way of example may be a commonly available battery powered reciprocating pump. Timed duty cycle operation for the pump preferably is under the control of a microprocessor circuit, which includes a plurality of manually selectable switch settings. The pump may be activated at one of a plurality of duty cycles or in a constant mode in response to a selected switch setting. A valve is actuatable during the pump operating periods to permit suction of the fluid from the evacuation tube entry to the reservoir. While the valve may be a pressure responsive valve, a solenoid valve is preferable as the latter permits a more direct control. By appropriate selection of the pump operating mode switch setting, a positive physiological pressure can be maintained at the joint wound while the medicinal solution is constantly administered thereto.

Figure 1:
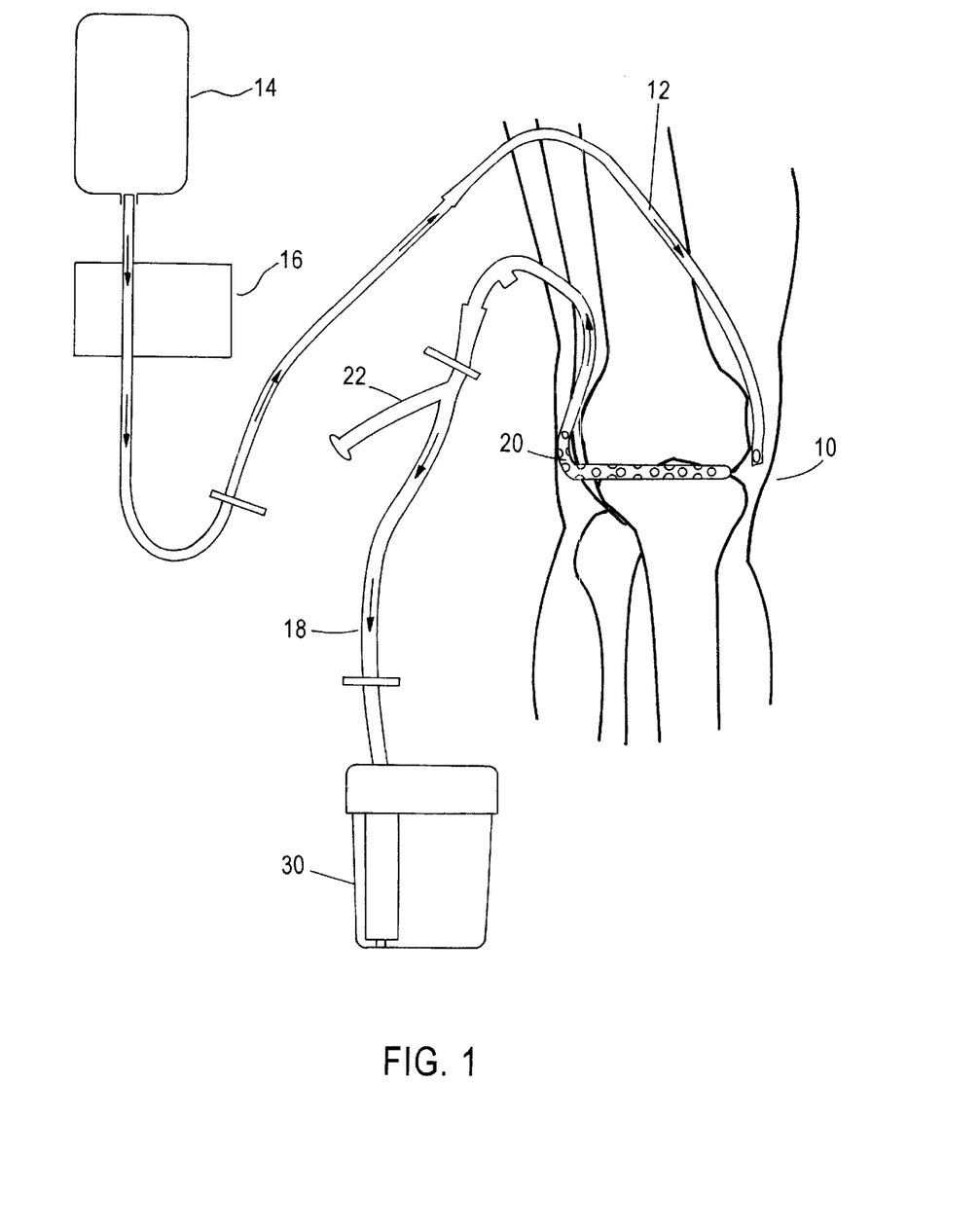
FIG. 1 is a simplified schematic diagram of a body joint wound treatment system in accordance with the present invention.

FIG. 1 is illustrative of the system of the invention as applied to a wound in knee area 10. It is to be understood that the knee joint is shown only by way of example and that the invention also is intended to be used for other body joint wounds including, but not limited to, larger joints such as the hip, medium sized joints such as the shoulder and smaller joints such as wrists, elbows, ankles etc.

Infusion tubing 12, shown inserted into the wound area, feeds a medicinal solution from an intravenous (I.V.) source 14 through I.V. pump 16 to irrigate the wound. The pump may be a standard commercially available device, such as manufactured for example, by Baxtor, I-VAC, Travenol, etc., and which is capable of providing pump rates up to about 999 cubic centimeters/hour (cc/hr), e.g., at least within a range of about 30 cc/hr to about 100 cc/hr.

During the irrigation period, the medicinal solution preferably contains anesthetic, anti-inflammatory, antibiotic and, optionally, anti-coagulant agents, as for example, Lidocaine, Solu-Cortef, Chloramphenicol and, optionally, Heparin. When the system is used for a blood collection function, a small amount of saline may be added to evacuation tubing 18 through self-sealing insert or injection site 22 to prevent blood clotting in the tubing. The evacuation tubing contains perforations in the end portion 20 that is shown inserted in the wound. Tubing 18 transports fluid from the wound to self contained reservoir and vacuum device 30. The reservoir ports and other features of reservoir and vacuum device 30 are illustrated in the more detailed diagrams of FIGS. 2–4.

Figure 2:
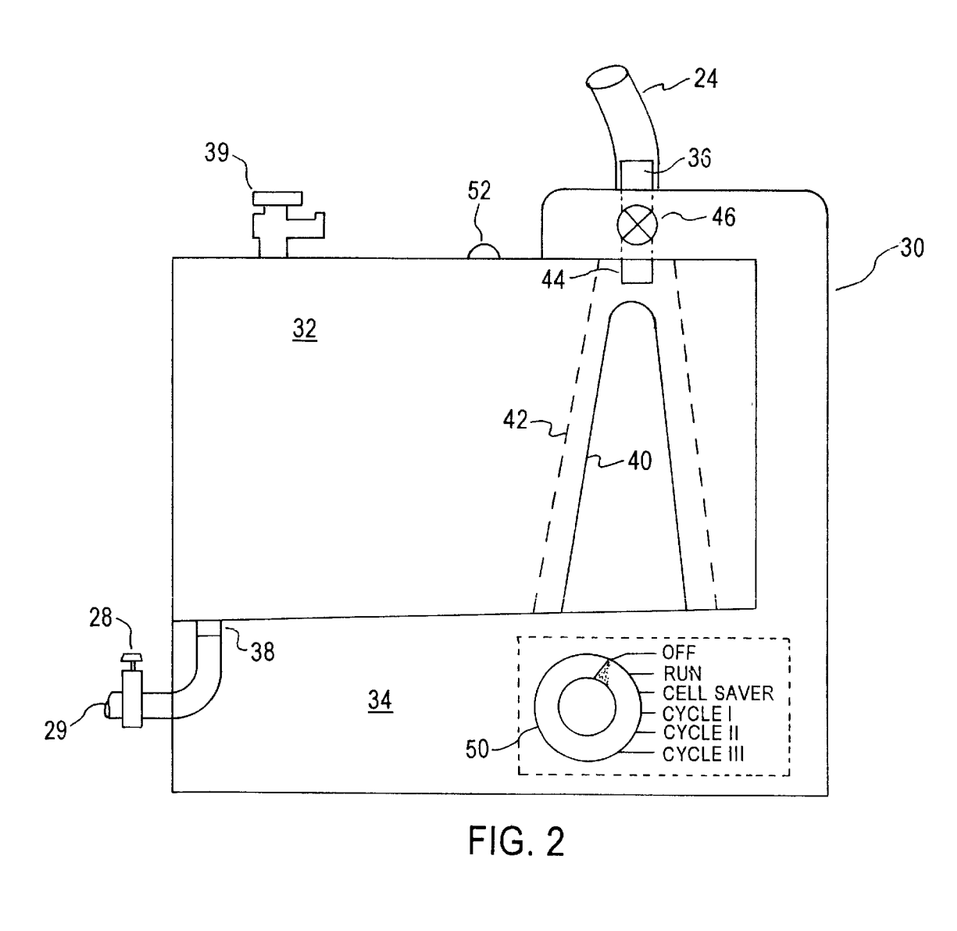
FIG. 2 is a more detailed front schematic view of the reservoir and vacuum device shown in FIG. 1.

FIG. 2 is a front perspective view of the reservoir and vacuum device structure 30, shown schematically. The structure comprises a fluid containing portion 32 and housing portion 34 in which the vacuum control apparatus is located. Container 32 preferably is made of transparent plastic material so that the level of the contents easily can be seen. Graduation marks, which can denote volume level, are shown along the left side of the container. The capacity of the reservoir preferably is of an order of about 750 cc. The housing portion 34 preferably is made of opaque material that can be made, for example, by injection molding.

The end portion 24 of the evacuation tube 18 through which blood is transported is coupled to fluid port 36 on the top of reservoir container 32. Clamp 28 is provided on tubing 29 that is coupled to a fluid exit port 38 in the bottom of the reservoir container. Pressure release valve 39 may be pushed when fluid is to be drained from the container through port 38. Valve 39 thus permits air to enter the container to equalize outside and inside pressures. A filter may be included to avoid entry of outside contaminants. Housing 34 contains a channel for passage of the tubing from port 38. The bottom of the container is sloped so that fluid readily can be fed by gravity flow to the exit port. Blood exiting the reservoir can be collected in a blood bag for reinfusion.

Inverted cone shaped structure 40 may be employed extending from the container bottom to a location proximate input port 44 at the top of the container. Blood entering therethrough will travel a short distance to the top of the cone and then down along the cone surface. The cone avoids damage to the blood cells that might otherwise occur if the blood were to traverse the entire distance in free fall. In the latter case, splattering or splashing is likely to occur, causing air to break up the cells. Filter 42, which surrounds the cone between the top and bottom of the container precludes passage of particles, such as clots or debris, therethrough to the reservoir.

Port 38, tubing 29 and clamp 28 also provide a means for draining the container of irrigation fluids transported from the wound. End portion 24 of the evacuation tube 18 is coupled to fluid input port 36 at the top of the reservoir housing 34. Structurally aligned in a vertical direction with port 36 are valve 46 and port 44. Valve 46, preferably a spring loaded solenoid valve, is operable to an open position to permit the flow of fluid from tube portion 24 to the container 32 during the irrigation/suction intervals. A pressure transducer in tubing 24 will electrically open the solenoid if pressure exceeds an A.A.B.B. prescribed limit.

Manually operable switch knob 50, which protrudes from the front of housing 34, can be set to one of several cycle operating mode positions or off and continuous run modes. Vacuum indicator 52 provides a visual indication of a vacuum condition. This device may comprise a transparent window to the periphery of which is sealed a flexible material. A vacuum level in the container sufficient for operation in a selected suction mode will cause an inward deflection of the material that is visibly recognizable from outside the reservoir container.

Figure 3:
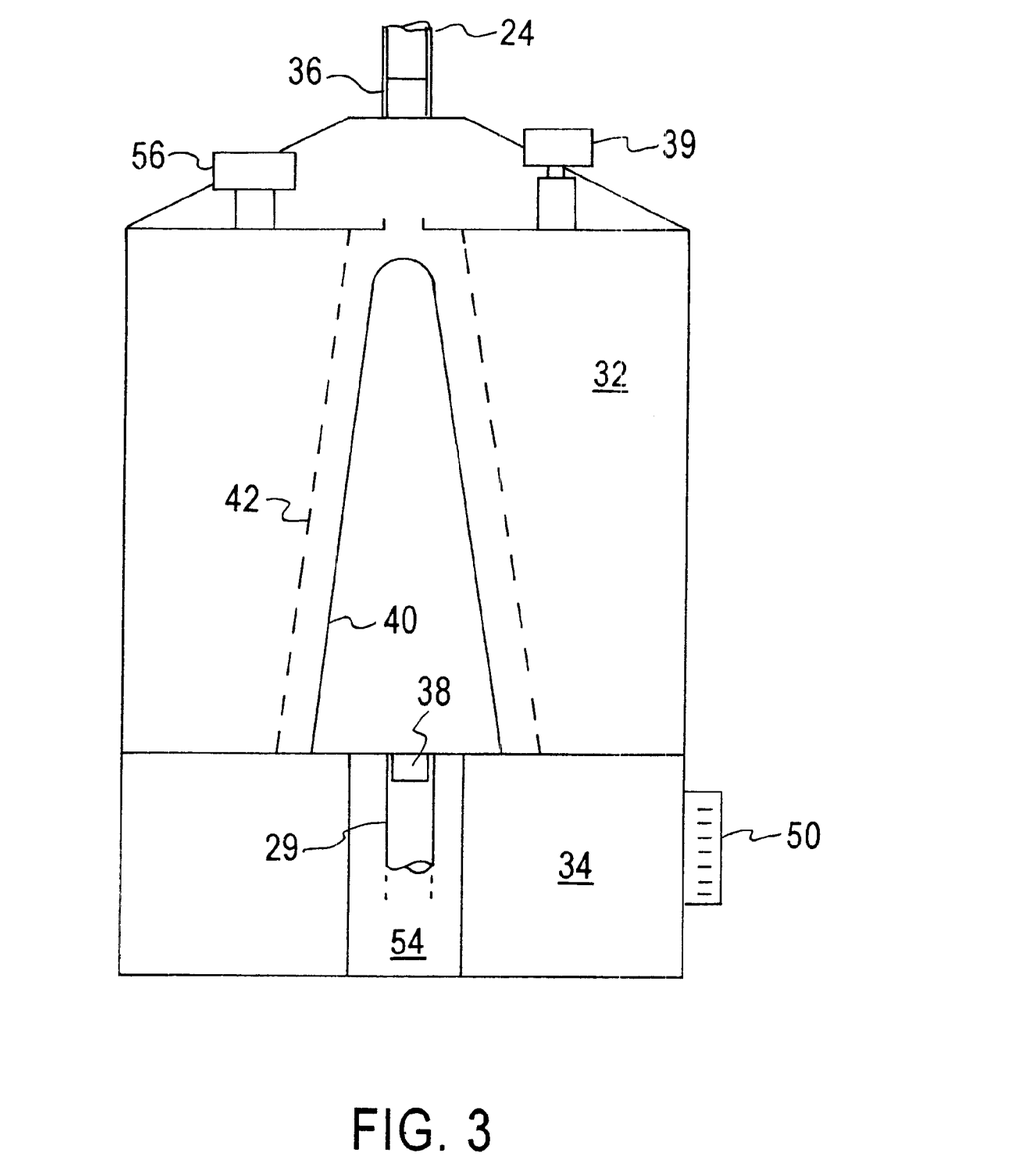
FIG. 3 is a left side schematic view of the reservoir and vacuum device.

FIG. 3 is a left side schematic view of the reservoir and vacuum device. Housing 34 contains a channel 54, recessed from its outer edge for passage of the tubing 29 from port 38. The channel, which extends to the bottom of housing 34, permits the tubing to emerge from the left side of the housing, as depicted in FIG. 2, or from the bottom. The device 30 thus can be placed on a horizontal surface or carried as the rehabilitating patient becomes mobile. A clip, not shown, may be attached to the housing for hanging from a hospital railing or the like. Port 56 permits connection of the reservoir to an alternative vacuum source, such as a wall source, common to hospital rooms. The port is provided with a cap and check valve to prevent entry of air into the reservoir.

Figure 4:
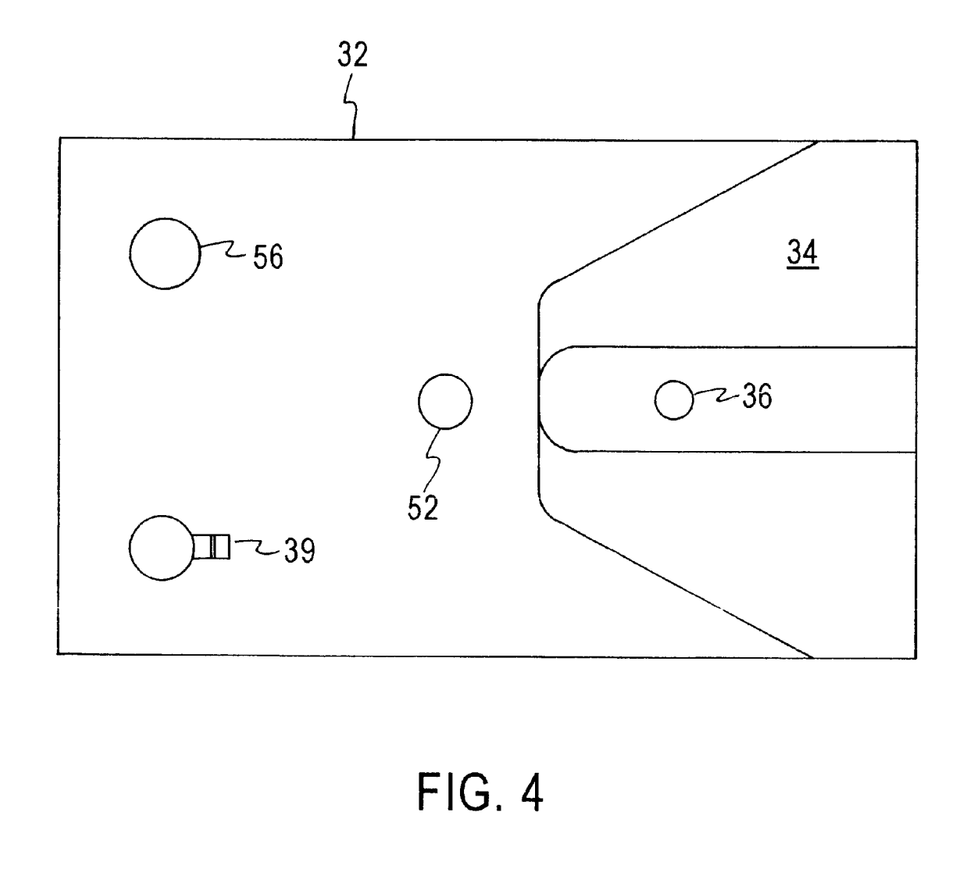
FIG. 4 is top schematic view of the reservoir and vacuum device.

FIG. 4 is a top view of the reservoir and vacuum device housing, illustrating the relative positions of the various elements previously described.

Figure 5:
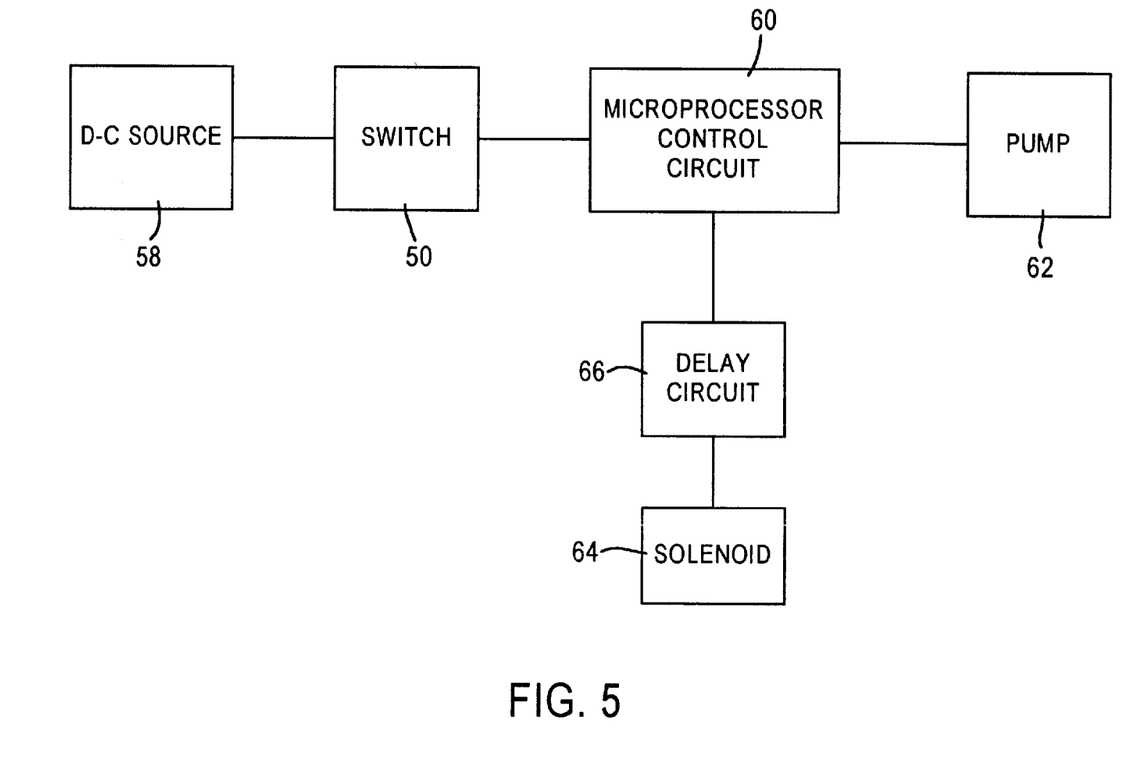
FIG. 5 is a simplified block diagram of a preferred control scheme in accordance with the present invention.

FIG. 5 is a simplified block diagram of a preferred control scheme of the vacuum device of the present invention that is contained in housing 34. Switch 50 is connected between a direct-current (d-c) source or an alternating-current (a-c) source and control circuit 60. Control circuit 60 preferably comprises a commercially available microprocessor timing circuit. While a single line is shown in the block diagram, it is to be understood that a plurality of connections are made from the various switch contact settings, illustrated in FIG. 2, to appropriate inputs of the microprocessor. The microprocessor provides control output signals to pump 62 and solenoid 64, the latter through delay circuit 66. Pump 62, when activated, creates the vacuum condition in the reservoir. Solenoid 64 is operative to control valve 46 at the input port 44 in housing 34. The time delay circuit may be of conventional design, such as a resistor-capacitor arrangement.

The plurality of switch positions correspond to the "OFF," "Cell Saver (CS)", "Cycle 1," "Cycle 2," "Cycle 3" and "Run" designations shown in FIG. 2. The "Run" setting represents continuous running operation. Except for the "OFF" condition, the other settings represent different on/off modes having respective duty cycles and cycle times. By way of example, Table 1 indicates preferred setting values.

TABLE 1

| Mode | Suction On | Suction Off | Cycle Time |
| --- | --- | --- | --- |
| CS | 05 minutes | 25 minutes | ½ hour |
| 1 | 10 minutes | 50 minutes | 1 hour |
| 2 | 20 minutes | 100 minutes | 2 hours |
| 3 | 30 minutes | 150 minutes | 3 hours |

In practicing the present invention, a single device is employed to perform a blood collection and blood saving function, followed by a wound irrigation function after surgery with a minimum of invasive insertions. In preferred operation, the CS (cell saver) mode is used immediately after surgery while the patient is losing at least about 80 ccs of blood and/or extra cellular fluid per hour without evidence of large clots.

This mode can be in place for about ten hours, while a solution containing Heparin and saline is infused to minimize blood clotting. In this mode, the switch of the inventive apparatus is set to the CS setting, whereby the microprocessor control circuit outputs a repetitive on/off duty cycle such as indicated in Table 1 for the CS mode. The solenoid will not be activated during this cycle as there is no connection therefrom to the CS switch contact. The CS mode is different then modes 1, 2, or 3 in that the solenoid vale remains open for gravity draining. The fluid from the wound therefore will gain entry to the reservoir at the input port 36. Blood entering the reservoir will impinge on the cone structure 40 and then traverse through by filter 42. Blood collected in the reservoir can be drained when the contents reach a desired volume level, which can be observed through the clear reservoir container. Drainage is achieved by manually operating pressure release valve 39 and opening clamp 28. Tubing 29 can be coupled at this time to a blood bag to be used for reinfusion. Thereafter, blood collection can continue in the CS mode, with the clamp 28 closed and the pressure release valve inactive.

The blood collection period will continue until the physician determines that bleeding has sufficiently diminished. Thereafter, the switch is set to one of the preset irrigation cycle settings (1–3) in accordance with what the physician deems appropriate for the type of wound being treated. At the outset of the selected cycle, the control circuit will output signals representing an on condition for the pump. In response, power is supplied to the pump which creates a vacuum in the reservoir.

In accordance with the present invention, a positive physiological pressure is maintained in the wound during the administration of medicinal solution and during the evacuation periods. Pressure in the entire wound is related to several variables including the rate of administering the medicinal solution, the volume of the wound or joint cavity and the cycle interval. These factors would all be taken into consideration by the artisan in determining the precise pump capacity and timed intervals to enable a comfortable positive physiological pressure in the wound and also to enable permeation of the medicinal solution.

The appropriate vacuum level in the reservoir is designed to allow a maximum of approximately 100 mm/Hg of pressure under the wound, a pressure level that conforms with A.A.B.B (American Association of Blood Banks) finding as to safety and comfort. Activation of solenoid 64 may be delayed from the initial switch setting for the cycle by delay circuit 66. The delay permits a sufficient vacuum to be established by pump 62 in the reservoir before the valve 46 will be opened to provide transport of the fluid from tube 24 to the reservoir container. Thereafter, the solenoid is activated and remains in this condition during the suction interval. The microprocessor control circuit will time out the suction on interval and then change the output control signals to deactivate the pump and solenoid for the timed suction off interval. This cyclic operation is repeated until the switch is set to the OFF or RUN position. Operation would occur in a similar manner for each of the other cycle modes.

In an alternative operative embodiment, the controlled vacuum in the reservoir can be constantly maintained at the appropriate level, i.e. approximately 100 mm/Hg, by use of a small vacuum pump and pressure transducer. The pump can be powered by a battery, an alternating-current (a-c) or a converted a-c. In this embodiment, the microprocessor will cyclically operate the solenoid in each of the selected mode cycles, without delay. As the desired pressure in the reservoir is maintained relatively constant, the delay circuit 66 can be eliminated or adjusted to zero delay. It can be appreciated that the present invention provides the advantage of portability because the device can be light weight, battery powered and self contained.

An advantage of the present invention is that a positive pressure is maintained in the joint to cause the wound and the area around the tubes to allow fluid to escape from the joint through the skin. This seepage keeps the bacteria count down in the wound and on the skin around the wound. Seepage not only cleans and relieves pain to the multiple layers of the wound and skin, but serves as a control valve maintaining a physiologically comfortable pressure in the wound area. The amount of seepage can be detected visually by inspection of the wound dressings. If the dressing appears too dry, the infusion rate of the medicinal solution can be increased an incremental amount as, for example, by about 10 cc/hr. If seepage appears too heavy, diminishment of the infusion rate by a similar amount would be appropriate. These adjustments may easily be implemented by controlling the I.V. pump to increase or decrease the rate of administering the medicinal solution to the patient.

Another advantage of the present invention, is related to reducing or eliminating the adverse affects associated with toxic accumulation of active agents which results from repeatedly or continuously administering the agents over a period of time. In accordance with the present invention, a pharmaceutical composition is prepared that has a relatively short peak effect, i.e. acts quickly to alleviate or minimize pain, and is relatively rapidly metabolized, or not absorbed in the gastrointestinal tract. The fast-acting, short-lived pharmaceutical composition is prepared by combining a local anesthetic, an anti-inflammatory agent and an antibiotic, wherein the local anesthetic has a peak effect no later than about 10 minutes, e.g. no later than about 5 minutes. Further, the present invention contemplates that the local anesthetic and anti-inflammatory each have a half-life of no greater than about 36 hours, e.g. no greater than about 8–12 hours. Given the guidance and objectives of the present disclosure, the optimum composition can be necessarily determined for administration to a patient in need of a particular treatment. In this regard, the interested reader is directed to, for example, Kings Guide (King Guide to Parental Mixture, edited by Patrick N. Catania, Ph.D., published by Pacemarq, Inc., 11701 Borman Drive Ste. 100, St. Louis, Mo.; 63146), which is used by pharmacies and pharmacologists to determine compatibility of drug mixtures, their peak effects, half-lives, etc.

A local anesthetic of the present invention, for example, can be selected from the group consisting of: Ambucaine, Amolanone, Amylocaine Hydrochloride, Benoxinate, Benzocaine, Betoxycaine, Biphenamine, Bupivacaine, Butacaine, Butamben, Butanilicaine, Butethamine, Butoxycaine, Carticaine, Chloroprocaine Hydrochloride, Cocaethylene, Cocaine, Cyclomethycaine, Dibucaine Hydrochloride, Dimethisoquin, Dimethocaine, Diperodon Hydrochloride, Dyclonine, Ecgonidine, Ecgonine, Ethyl Chloride, Etidocaine, β-Eucaine, Euprocin, Fenalcomine, Fornocaine, Hexylcaine Hydrochloride, Hydroxytetracaine, Isobutyl p-Aminobenzoate, Leucinocaine Mesylate, Levoxadrol, Lidocaine, Mepivacaine, Meprylcaine, Metabutoxycaine, Methyl Chloride, Myrtecaine, Naepaine, Octacaine, Orthocaine, Oxethazaine, Parethoxycaine, Phenacaine Hydrochloride, Phenol, Piperocaine, Piridocaine, Polidocanol, Pramoxine, Prilocaine, Procaine, Propanocaine, Proparacaine, Propipocaine, Propoxycaine Hydrochloride, Pseudococaine, Pyrrocaine, Ropivacaine, Salicyl Alcohol, Tetracaine Hydrochloride, Tolycaine, Trimecaine, Zolamine, their pharmaceutically acceptable salts, or mixtures thereof.

The anti-inflammatory agent of the present invention can comprise at least one glucocorticoid, or a pharmaceutically acceptable salt thereof. For example, a glucocorticoid anti-inflammatory agent can be selected form the group consisting of: 21-Acetoxypregnenolone, Alclometasone, Algestone, Amcinonide, Beclomethasone, Betarnethasone, Budesonide, Chloroprednisone, Clobetasol, Clobetasone, Clocortolone, Cloprednol, Corticosterone, Cortisone, Cortivazol, Deflazacort, Desonide, Desoximetasone, Dexamethasone, Diflorasone, Diflucortolone, Difluprednate, Enoxolone, Fluazacort, Flucloronide, Flumethasone, Flunisolide, Fluocinolone Acetonide, Fluocinonide, Fluocortin Butyl, Fluocortolone, Fluorometholone, Fluperolone Acetate, Fluprednidene Acetate, Fluprednisolone, Flurandrenolide, Fluticasone Propionate, Formocortal, Halcinonide, Halobetasol Propionate, Halometasone, Halopredone Acetate, Hydrocortamate, Hydrocortisone, Loteprednol Etabonate, Mazipredone, Medrysone, Meprednisone, Methylprednisolone, Mometasone Furoate, Paramethasone, Prednicarbate, Prednisolone, Prednisolone 25-Diethylamino-Prednisolone Sodium Phosphate, Prednisone, Prednival, Prednylidene, Rimexolone, Tixocortol, Triamcinolone, Triamcinolone Acetonide, Triamcinolone Benetonide, Triamcinolone Hexacetonide, their pharmaceutically acceptable salts, or mixtures thereof.

The antibiotic of the present invention can be selected, for example, from the group consisting of: aminoglycosides; amphenicols, such as Chloramphenicol; betalactams, such as cephalosporins, e.g. cephalosproin, cefazolin, ceftazidime, etc.; lincosamides; macrolides; polypeptides; tetracyclines; synthetic antibiotics, such as septazine; their pharmaceutical salts; and mixtures thereof.

Optionally, the pharmaceutical composition of the present invention further comprises an anticoagulant. The anticoagulant can be selected from the group consisting of: Acenocoumarol, Ancrod, Anisindione, Bromindione, Clorindione, Coumetarol, Cyclocumarol, Dextran Sulfate Sodium, Dicumarol, Diphenadione, Ethyl Biscoumacetate, Ethylidene Dicoumarol, Fluindione, Heparin, Hirudin, Lyapolate Sodium, Oxazidione, Pentosan Polysulfate, Phenindione, Phenprocoumon, Phosvitin, Picotamide, Tioclomarol, Warfarin, their pharmaceutically acceptable salts, or mixtures thereof.

In practicing the invention, a medicinal solution is prepared from the pharmaceutical composition by admixing the pharmaceutical composition in a pharmaceutically acceptable carrier. In embodiment of the present invention, a medicinal solution comprising about 0.01 to about 5 weight percent of a local anesthetic, about 0.01 to about 5 weight percent of an anti-inflammatory agent, about 0.01 to about 5 weight percent of an antibiotic and a carrier, e.g. sterile water, can thus be prepared. Optionally, an anticoagulant is added to the medicinal solution. It is understood that the active ingredients of the present invention are not necessarily completely dissolved in the carrier. The present invention contemplates heterogeneous mixtures and/or emulsions in formulating the medicinal solution. The weight percent expressed in the present invention refers to the weight of the component to the total weight of the composition.

In administering the medicinal solution of the present invention, it is believed that the mechanism of action of the local anesthetic stabilizes the neuronal membrane when administered to a wound by inhibiting the ion fluxes required for the initiation and conduction of an impulse thereby effecting local analgesic action. In an embodiment of the present invention, the local anesthetic is selected from the group consisting of: benzocaine, bupivacaine, butamben picrate, cocaine, dibucaine, lidocaine, tetracaine, their pharmaceutical salts, and mixtures thereof.

Advantageously, the half-live, or metabolism of the local anesthetic of the present invention is relatively short, such that the medicinal solution can be continuously administered without adverse side effects to the treated patient. In accordance with the present invention, the local anesthetic is metabolized rapidly by the liver and secreted thereupon through the kidneys. For example, the half-life of Lidocaine is about 1 and ½ hours to about 2 hours. The maximum suggested dose of Lidocaine, is about 300 mg I.V. every 90 minutes. Assuming that the inventive solution comprises about ⅛% of Lidocaine (i.e. about 1250 mg in 1000 ccs of saline solution) and is administered at a rate of about 70 cc/hr and the patient absorbed 100% of the Lidocaine in the solution over a 90 minute period, the patient would receive a dose of about 135 mg of Lidocaine. Such a dose is well within the framework of safety and, hence, repeated or continual doses of Lidocaine can be safely administered with the given concentration.

It is known that much larger doses of certain local anesthetics can be used without ill effects. For example, Edmondson, et al. administered 50 to 100 mg of Lidocaine I.V. to patients over a 40 to 120 second period without ill effects for post-stroke pain. Edmondson, Simpson, Stubler and Beric, "Systemic Lidocane Therapy for Post-Stroke Pain" Southern Medical Journal (1993) 86(10):1093–1096. An article written by Pinzur et al. asserted that 0.5% of Bupicocaine was injected by continuous perineural infusion around the major nerve following amputation of the lower limb and reported good relief of pain. Pinzur, Gupta and Pluth "Continuous Post-Operative Infusion of Regional Anesthetic After Amputation of Lower Extermity" Journal of Bone and Joint Surgery (1996) 42:282–287. The use of Marcaine was also reported for relief of pain following cancer surgery of the lower extremity. However, through experimentation, it was discovered that if the dosage of Marcaine is not more or less strictly monitored, critical complications can occur.

In an embodiment of the present invention, the anti-inflammatory agent is one or more glucocorticoid or pharmaceutically acceptable salts thereof. Glucocorticoids are known for their anti-inflammatory characteristics and for preventing swelling, relieving pain from the swelling and preventing erythema. Cortisteroids stabilize phospholipids found in cell membranes by blocking the release of arachidonic acid and thus inhibiting the next metabolic step of arachidonic acid to prostaglandins, which in turn causes prolonged pain and swelling in local tissues following trauma or surgery. In this regard, Cortisone is known for its anti-inflammatory characteristics. Hydrocortosone Sodium Succinate also is know to relieve swelling and pain by stopping the production of prostaglandins. Further, Betamethasone has approximately 25 times more anti-inflammatory characteristics than Hydrocortisone Sodium Succinate (Solu-Cortef) and is a widely used anti-inflammatory with few side effects.

In accordance with the present invention, the anti-inflammatory advantageously is administered in the medicinal solution such that the agent does not adversely accumulate in the patient's system, e.g. the half-live of the anti-inflammatory is no greater than about 36 hr. In an embodiment of the present invention, the anti-inflammatory is selected from the group consisting of: Glucocorticoids, such as Cortisone, Hydrocortisone, Prenisone, Prenisolone, Triamcinolone, Methylpredenisolone, their pharmaceutically acceptable salts and mixtures thereof.

Solu-Cortef (Hydrocortosone Sodium Succinate) can be used in the medicinal preparation of the present invention. Solu-Cortef has an initial rapid action, is soluble in saline, compatible with the other drugs contemplated in the medicinal solution of the present invention and its duration of activity suppression is only about 1.5 days. The action of Hydrocortosone Sodium Succinate lasts only about 1-¼ to 1-½ days. As far as dosage safety, the Physicians Desk Reference reports that about 100 to 500 mg of Solu-Cortef can be administered I.V. every three to four hours; therefore, the patient could conceivably be given 1200 mg over a twenty-four hour period without adverse effects. Assuming that the present inventive solution comprises 0.04% of Solu-Cortef (i.e about 400 mg in 1000 ccs of saline solution) and is administered at a rate of 70 cc/hr over a 24 hour period, the maximum dose the patient would receive, if 100% was absorbed, would be about 600 mg of Solu-Cortef which is well within the safe dosage amounts for this anti-inflammatory.

Larger dosages of the anti-inflammatory can also be used in the present invention. For example, Watanukit et al. reported administering 1 gm of Solu-Cortef or Solumedrol inter-operatively to patients after total hip or knee joint replacements. Watanuki et al. "The effect of Steroids on Post-Operative Pain and Pyrexia" Maumasui (1991) vol. 40(4):570–3. In this study, it was reported that allegedly 95% of the patients suffered post-operative pain without interoperative steroid administration, whereas only 33% of the patients with total hip or knee joint replacements experienced pain with interoperative steroid administration. The reference, therefore, recognizes single dose administration of steroids to relieve pain.

There are risks associated with the use of cortisteroids in patients with diabetes, blood pressure elevation, or severe infections. However, the use of cortisteroids is not contraindicated with all patients. Thus, it is advisable to closely monitor patients with a sliding scale program for diabetics, careful blood pressure checks and resumption of blood pressure medication after surgery for patients with hypertension, and appropriate antibiotics for systemic infection.

In an embodiment of the present invention, a broad spectrum antibiotic is selected from the group consisting of: Chloramphenicol, Cephalosporin, Cefazolin, Ceftazidime, their pharmaceutical salts and mixtures thereof. Chloramphenicol is a very good broad spectrum antibiotic that has been used since the early 1960s as effective in preventing infections. It is a very effective broad-spectrum antibiotic against the common bone and joint infections. Chloramphenicol has one draw back, however. It should not be used in patients with blood dyscrasias. It has been reported to have caused aplastic anemia and other blood problems. Hence, it is suggested that Chloramphenicol not be used for a sustained period of time because of the possibility of aplastic anemia for such patients.

In an embodiment of the present invention, a medicinal solution comprising Chloramphenicol can be prepared such that the patient receives only about 1-½ gm in a 24 hour period. Thus, if 100% was absorbed during the 24 hour period while treating a wound as, for example, following a total knee arthroplasty, the administered 1 ½ gm over a 24 hour is a safe dose, in fact, for three days. Since, however, only approximately 40% of the antibiotic is typically absorbed, the amount that is available to the bone marrow is, thus, very small. For patients with blood dyscrasias a dose of about 2 gm of Cephalosporin or a dose of about 1 gm Septaz can be used in place of a dose of about 1 g of Chloramphenicol for the 24 hour period.

In addition to the local anesthetics anti-inflammatory and antibiotic, the medicinal solution further comprises an anticoagulant. In an embodiment of the present invention, Heparin or a pharmaceutically acceptable salt thereof is added to the medicinal solution. Heparin is compatible in a solution comprising Solu-Cortef, Lidocaine and Chloramphenicol up to 1000 units of Heparin per thousand ccs of saline. For example, 1000 units of Sodium Heparin can be added to 1000 cc of normal saline when the medicinal solution is contemplated for use in treating large joints (such as a knee), 500 units of Heparin can be added to 500 cc normal saline for smaller joints, and 500 units of Heparin can be added to 250 cc normal saline in even smaller wounds. Due to the fact that 1000 units of Heparin with 1 gm of Cefazolin is compatible for 24 hours, a weaker broad-spectrum antibiotic coverage than the Chloramphenicol, the preferred amount would be 2 gm of Cefazolin. This is why, when using Cefazolin as a substitute for Chloramphenicol in large joints, only 1 gm can be used, in the small or mid-sized joints only 500 units can be used, and in small wounds only 250 mg of Cefazolin can be used. Therefore, there is not a very strong antibiotic coverage when substituting Cefazolin for Chloramphenicol. For better coverage under these circumstances it is recommended that Fortaz or Septaz (generically Ceftazidime) be used. This is generically Ceftazidime. Bacterial coverage is very good for gram negative organisms and for many gram positive organisms which include staphylococcus aureus and staphylococcus epidermidis. There is a warning for cross hypersensitivities to patients with sensitivities to Cephalosporins, Penicillins and Ceftazidimes. The recommended application of this would be 1 gm of Septaz per 1000 for large joints, 500 mg of Septaz for intermediate size joints, and 500 mg of Septaz for smaller joints.

EXAMPLES

A medicinal solution was prepared by combining about 0.05 to about 0.5 weight percent of a local anesthetic, about 0.02 to about 0.2 weight percent of an anti-inflammatory, about 0.05 to about 0.5 weight percent of an antibiotic, and optionally, a glucocorticoid with the remainder of the composition comprising normal saline, i.e. 0.9% sodium chloride in sterile water. The medicinal solutions were then administered directly at a relatively constant rate to a joint after a surgical operation. During administration of the medicinal solution to the wound, fluid and debris were periodically removed by suctioning the wound. Table 2 lists exemplary medicinal solutions, rates of administrations, vacuum cycles for treating a particular joint size with the wound treating system of the present invention over a period of up to three days.

TABLE 2

| Joint Size | Pharmaceutical Compositions | Rate of Administration | Vacuum Cycle |
|---|---|---|---|
| Large Joints (Hip or Knee) | 1) 1000 cc normal saline<br>2) 1250 mg Lidocaine<br>3) 400 mg Solu-cortef<br>4) 1 g Chloramphenicol or cephalosporin or septaz<br>5) up to 1000 units Heparin | about 50 cc/hr to about 70 cc/hr | about 30 min Suction On about 150 min Suction Off |
| Medium Joints (Shoulder) | 1) 500 cc normal saline<br>2) 1250 mg Lidocaine<br>3) 400 mg Solu-cortef<br>4) 1 g Chloramphenicol or cephalosporin or septaz<br>5) up to 500 units Heparin | about 25 cc/hr to about 40 cc/hr | about 20 min Suction On about 100 min Suction Off |
| Small Joints (Elbow, Ankle, Rotary Cuff wounds) | 1) 250 cc normal saline<br>2) 1250 mg Lidocaine<br>3) 300 mg Solu-cortef<br>4) 500 mg Chloramphenicol or cephalosporin or septaz<br>5) up to 500 units Heparin | about 20 cc/hr to about 30 cc/hr | about 20 min Suction On about 70 min Suction Off |

In cases of blood dyscrasia or allergy, Cephalosporin or Ceftazidime (i.e. Septaz) will be used in place of Chloramphenicol as follows: large joints 1 gm, medium and small joints 0.5 gm of the Cephalosporin or Septaz.

The above prepared medicinal solutions were then used to relief pain, swelling and irrigate the knees of human patients that had undergone total knee arthroplasties. After surgery, the patients were fitted with the wound treatment system of the present invention, as illustrated in FIG. 1. It was determined that several factors affect leakage through the wound including wound closure resistance and knee capacity variations among different patients.

The pressure of the patients' knees after surgery without a tourniquet and after the knees were evacuated of blood and fluid was between about 9–14 mmHg, which coincides with the normal tissue tension of about 10–15 mmHg. Addition of about 75–125 cc of the medicinal solution at a rate of about 100 cc/hr to the knees increased the measured pressure in the knees from about 16 to about 22 mmHg without the observation that the solution was leaking from the closed wounds. When about 100 to about 150 cc of medicinal solution was administered, the measure pressure in the wounds ranged from about 18 to about 26 mmHg with observable leaking of fluid. The wounds were then dressed with a curlex and ace bandage which increased the pressure in the wound to about 25–33 mmHg and significantly reduced fluid leaking from the wound. The addition of about 150–175 cc of medicinal solution to the wound resulted in observable leaking and a sustained pressure of about 32–40 mmHg in the wound.

Seepage of the medicinal solution through the wound to the skin surface prevented the pressure from reaching above about 40 to about 50 mmHg in the wound. The solution escaped around the wound sutures and around the tubing used in the system preventing contamination and/or bacteria from entering the wound. Thus, a comfortable positive physiological pressure in the wound with permeation of the medicinal solution was achieved with an administration rate as high as 100 cc/hr.

At regular intervals, fluid from the patient's knee was extracted, as shown in Table 2. Cyclic suctioning of fluids from the wound minimizes the build-up of blood, dead tissue, debris, bacteria, extracellular fluid, etc. Cyclic suctioning of fluids further removes medicinal solution that has been separately infused in the wound and that has become depleted and/or impotent over time because of its fast-acting, short-lived nature.

The effectiveness of the medicinal solution employing the apparatus shown in FIG. 1 is found in Table 3. After undergoing a bilateral simultaneous total knee arthroplasty surgical procedure, the patients were treated by either conventional epidural analgesia or narcotics IV/IM or by administering the medicinal solution of the present invention. As shown in Table 3, patients treated with the medicinal solution of the present invention using the treatment apparatus as shown in FIG. 1 resulted in a decrease of about 4.5 days in the average hospital stay, a 300 to 900% decrease in the amount of Morphine used to control pain in the patient and about a 200% increase in knee motion in 3 days

TABLE 3

| Method of Treatment | No of patients | Average Hospital Stay (Days) | Average Dose (mg) of Pain medication | | Average Knee Motion on Day 3 |
|---|---|---|---|---|---|
| | | | Day 2 | Day 3 | |
| Epidural Analgesia | 3 | 9.0 | 58.3 | 31.6 | 58.3 degrees |
| Narcotics IV/IM or | 3 | 14.3 | 40.0 | 41.6 | 45 degrees |
| K-cycle | 4 | 4.5 | 0 | 0 | 90 degrees |

Thus, as disclosed by the present examples, the relief of pain, swelling and irrigation of a wound following knee surgery can be simultaneously achieved by administering medicinal solution comprising a local anesthetic, an anti-inflammatory and an antibiotic to permeate and leak though the wound to the skin surface while debris and contaminants are removed by periodically suctioning fluids from the wound.

In this disclosure there is shown and described only the preferred embodiments of the invention and but a few examples of its versatility. It is to be understood that the invention is capable of use in various other combinations and environments and is capable of changes or modifications within the scope of the inventive concept as expressed herein. For example, while the preferred embodiment has been described as applicable to various surgical joint wounds, the invention would have use in other body wounds with minor modifications that would be within the skill of the practitioner.

What is claimed is:

1. A medicinal solution, comprising about 0.01 to about 5 weight percent of at least one local anesthetic, about 0.01 to about 5 weight percent of at least one anti-inflammatory, about 0.01 to about 5 weight percent of at least one antibiotic, at least one anticoagulant, and a carrier;

wherein the at least one local anesthetic, anti-inflammatory, antibiotic, anticoagulant, and the carrier are, respectively, Lidocaine or a pharmaceutical salt thereof, Hydrocortisone sodium succinate, Chloramphenicol or a pharmaceutical salt thereof and Heparin or a pharmaceutical salt thereof in normal saline.

2. A method of treating a wound of a mammal, the method comprising:

administering the medicinal solution of claim 1 to the wound to treat the wound.

3. The method according to claim 2, comprising directly administering the medicinal solution continuously at a relatively constant rate to the wound.

4. The method according to claim 2, comprising administering the medicinal solution continuously at a rate of about 20 cc/hr to about 100 cc/hr.

5. The method according to claim 2, comprising administering the medicinal solution over a period up to about 3 days.

6. The method according to claim 2, further comprising the step of:

maintaining a relatively constant positive physiological pressure in the wound during and throughout said administration step.

* * * * *